PLANT GROWTH REGULATORS

The present invention relates to new and valuable agents for influencing plant growth, based on compositions containing morpholinium or piperidinium salts and substituted carboxylates of 3-phenoxybenzyl, and processes for influencing plant growth with these agents.

It is known to use N,N-dimethylmorpholinium chloride (German Printed Application DAS No. 1,642,215), N,N-dimethylpiperidinium chloride (German Laid-Open Application DOS No. 2,207,575), N,N-dimethylpyrrolidinium chloride and N,N-dimethylhexahydropyridazinium bromide as growth regulators. Reduction in growth height is one of the effects achieved with these active ingredients.

I have now found that agents for influencing plant growth based on a substituted heterocyclic N,N-dimethylammonium salt selected from the group consisting of the N,N-dimethylmorpholinium salt, the N,N-dimethylpiperidinium salt, the N,N-dimethylpyrrolidinium salt and the N,N-dimethylhexahydropyridazinium salt have an improved biological action if they additionally contain a compound selected from the group of substituted carboxylates of 3-phenoxybenzyl of the formulae

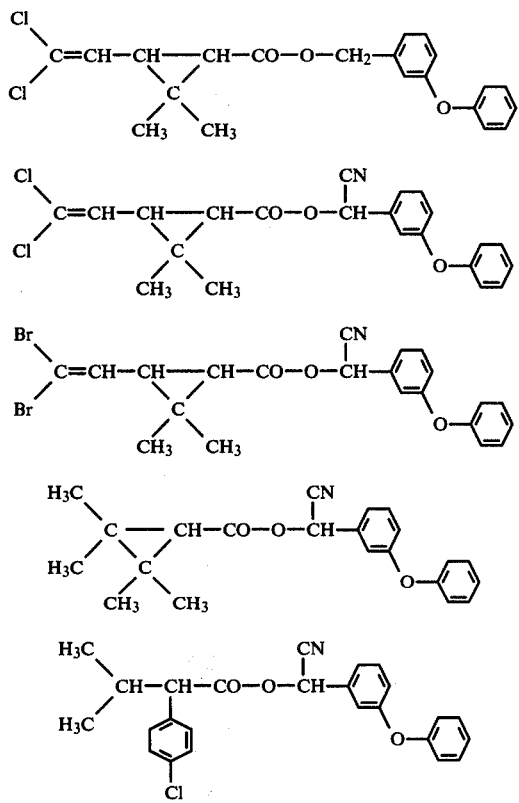

The agents may contain two or more of the above-mentioned active ingredients. The carboxylates may also be in the form of their various isomers, e.g., cis-trans isomers or optical isomers, or mixtures thereof.

Preferred salts of the substituted heterocyclic N,N-dimethylammonium compounds are the halides, for example the bromides and, preferably, the chlorides.

The ratio of one or more salts from the group of the substituted heterocyclic N,N-dimethylammonium salts to one or more active ingredients from the group of the carboxylates may vary within wide limits, for instance from 1:10 to 20:1 or from 1:8 to 12.9:1 parts by weight. Compositions having a weight ratio of from 1:2 to 1.6:1 also have a good effect. The agents according to the invention act on plants such as cereals and cotton. The action achieved by the compositions according to the invention is superior to that obtained by adding together the individual actions of their components, i.e., it is synergistic. This synergistic action is particularly evident in the case of cotton, where a considerable reduction in height is achieved. Additional effects are also observed, for instance the desired abscission of foliage shortly before the bolls are ripe, and an increase in yield, for example as a result of the greater weight of the individual bolls. The compounds from the group of the carboxylates also have an insecticidal action. Application rates for the agents according to the invention range for instance from 50 to 500 g of active ingredient composition per hectare. The compositions according to the invention may for example in the case of cotton be applied shortly before or shortly after the onset of flowering. In certain areas, a second treatment is, depending on the weather conditions, advantageous during full blossom and up to the end of the bloom period. The agents may also be used as seed dressings or for treating the soil before or after emergence of the plants.

Application may be effected for instance in the form of directly sprayable solutions, powders, suspensions, dispersions, emulsions, oil dispersions, pastes, dusts, broadcasing agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, etc. and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ether, condensation products of sulfonated naphthalene and naphthalene derivatives with formaldehyde, condensa-

United States Patent [19]

Kappel

[11] 4,153,445

[45] May 8, 1979

[54] PLANT GROWTH REGULATORS

[75] Inventor: Ernst Kappel, Dudenhofen, Fed. Rep. of Germany

[73] Assignee: BASF Aktiengesellschaft, Ludwigshafen, Fed. Rep. of Germany

[21] Appl. No.: 872,316

[22] Filed: Jan. 25, 1978

[30] Foreign Application Priority Data

Feb. 7, 1977 [DE] Fed. Rep. of Germany ....... 2704962

[51] Int. Cl.$^2$ .......................... A01N 9/02; A01N 9/22
[52] U.S. Cl. ........................................... 71/94; 71/88; 71/92; 71/95; 71/105; 71/106
[58] Field of Search ................. 71/88, 92, 94, 95, 105, 71/106

[56] References Cited

U.S. PATENT DOCUMENTS

| | | | |
|---|---|---|---|
| 3,895,933 | 7/1975 | Jager | 71/94 |
| 3,905,798 | 9/1975 | Zeeh et al. | 71/95 X |
| 4,014,678 | 3/1977 | Huppi et al. | 71/94 |
| 4,040,813 | 8/1977 | Newhall | 71/106 X |
| 4,057,413 | 11/1977 | Naumann et al. | 71/92 X |
| 4,059,435 | 11/1977 | Johnson | 71/88 X |
| 4,071,551 | 1/1978 | Jung et al. | 71/94 X |

*Primary Examiner*—Joseph Paul Brust
*Attorney, Agent, or Firm*—Keil & Witherspoon

[57] ABSTRACT

New agents for influencing plant growth and based on a composition of (a) a substituted heterocyclic ammonium salt and (b) a substituted carboxylate of 3-phenoxybenzyl, and processes for influencing plant growth with these agents.

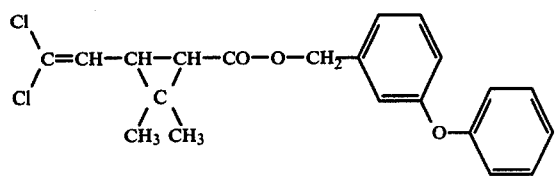
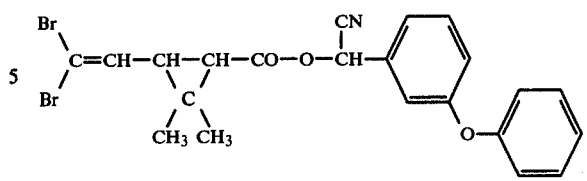
wherein the ratio of (a) to (b) is from 1:10 to 20:1.
2. An agent for influencing plant growth, comprising a composition of (a) N,N-dimethylpiperidinium chloride and (b) 3-phenoxybenzyl-(+)-cis-trans-2,2-dimethyl-3-(2,2-dichlorovinyl)-cyclopropane carboxylate, wherein the ratio of (a) to (b) is from 1:10 to 20:1.
* * * * *
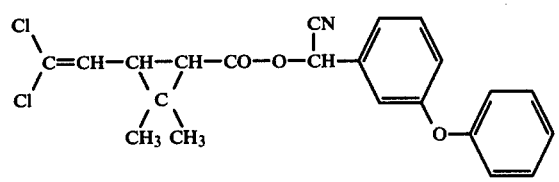

2 Claims, No Drawings